United States Patent [19]
Johnson, Jr. et al.

[11] Patent Number: 5,213,564
[45] Date of Patent: May 25, 1993

[54] PROPHYLACTIC ANKLE BRACE

[75] Inventors: Glenn W. Johnson, Jr., Summit; Henry J. McVicker, Chatham, both of N.J.

[73] Assignee: Aircast, Inc., Summit, N.J.

[21] Appl. No.: 821,401

[22] Filed: Jan. 14, 1992

[51] Int. Cl.[5] ............................................. A61F 3/00
[52] U.S. Cl. ................................................... 602/27
[58] Field of Search .................... 602/27, DIG. 20; 128/80 H, 80 F, 80 E

[56] References Cited

U.S. PATENT DOCUMENTS

| 4,280,489 | 7/1981 | Johnson, Jr. | |
|---|---|---|---|
| 4,510,927 | 4/1985 | Peters | |
| 4,665,904 | 5/1987 | Lerman | 602/27 |
| 4,834,078 | 5/1989 | Biedermann | 602/27 |
| 5,031,607 | 7/1991 | Peters | 602/27 |

Primary Examiner—Richard J. Apley
Assistant Examiner—Beverly A. Meindl
Attorney, Agent, or Firm—Jones, Day, Reavis & Pogue

[57] ABSTRACT

A prophylactic ankle brace for protecting the ankle of paratroopers and which fits on the outside of the paratrooper boot. It includes lateral and medial side walls extending longitudinally upwardly to encompass the ankle and lower extremity of the leg above the ankle with a substantially U-shaped member connecting the spaced apart side walls for extending substantially around and conforming to the back of the shoe to hold the side walls in fixed relationship to each other and to the shoe. Straps are provided for removably attaching the connected side walls to the shoe and to the lower extremities of the leg in fixed relationship.

12 Claims, 2 Drawing Sheets

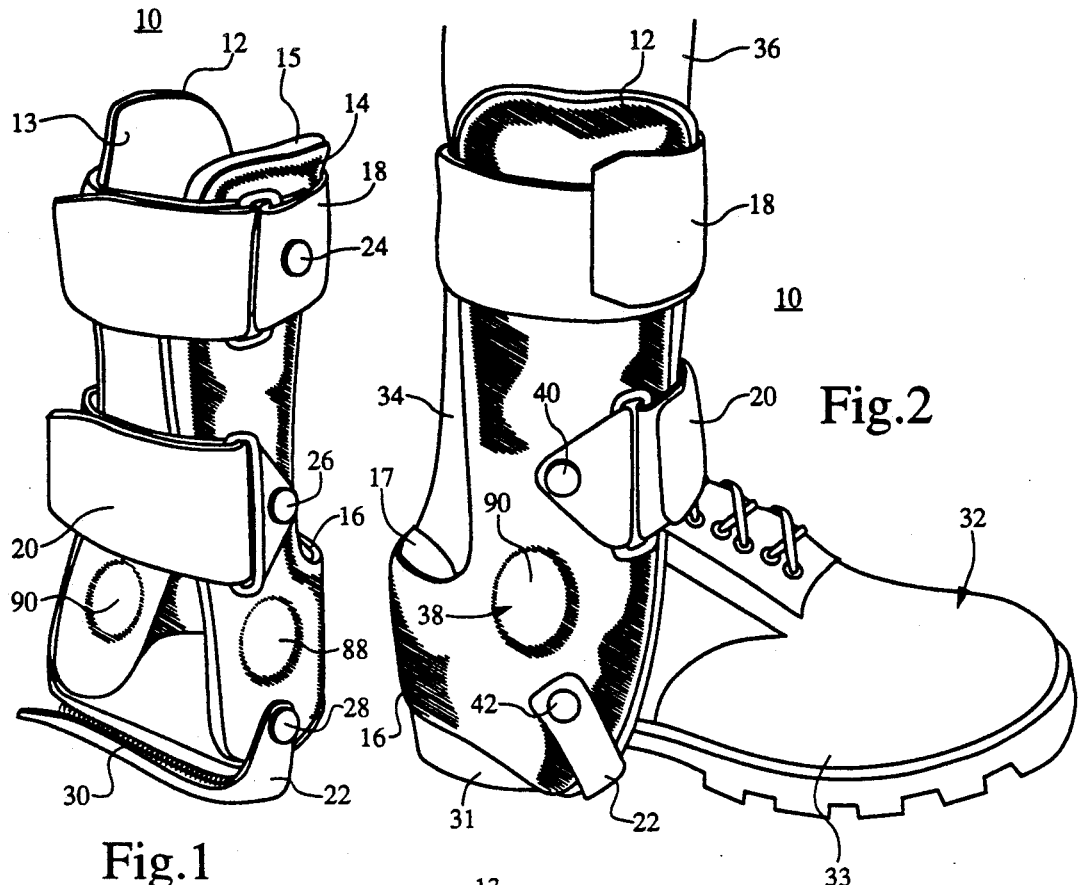
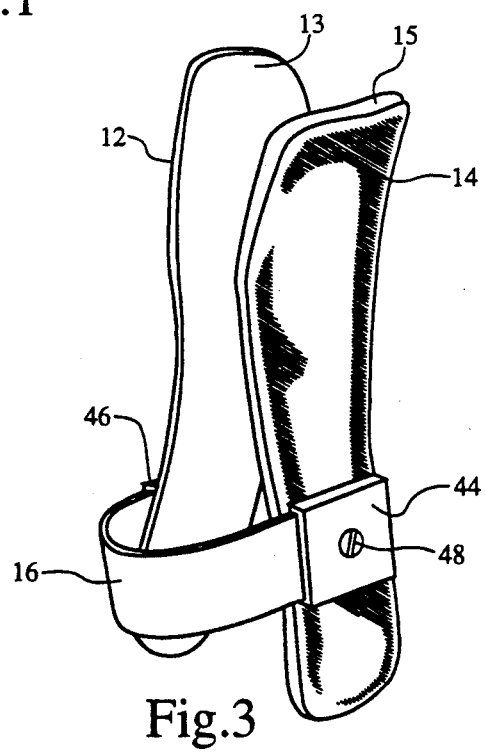

PROPHYLACTIC ANKLE BRACE

FIELD OF THE INVENTION

The present invention relates generally to orthopedic ankle braces for stabilizing the ankle against inversion and eversion without limiting normal plantarflexion and dorsiflexion of the ankle and in particular relates to such ankle brace for use with a boot to protect the ankles of those such as paratroopers who apply large inversion forces to the ankle.

BACKGROUND OF THE INVENTION

It is known that when paratroopers strike the ground with their inordinate weight due to equipment that they carry, large forces are applied to the ankle with a large number of ankle injuries caused by excessive inversion or eversion of the ankle. Such ankle injury rate is significant and of major concern.

In the process of developing a brace that could be worn in a combat boot and provide ankle protection during a parachute landing, a device was used such as disclosed in U.S. Pat. No. 4,280,489. However, in a recent trial with several hundred paratroopers, it became clear that the bulk of the device located within the boot was more than the average paratrooper would accept unless he had a history of ankle injuries. An effort was made to apply such a device on the outside of a boot to provide protection during the jump and provide quick removal on the ground for disposal with the chute. However, the device disclosed in U.S. Pat. No. 4,280,489, when applied to the outside of the boot, provided little inversion resistance. The two sides of the device shifted on the boot and buckled from lack of support from the shoe.

The present invention overcomes the disadvantages of the prior art and includes lateral and medial plastic supports that are of similar shape and contour to those disclosed in U.S. Pat. No. 4,280,489 which is incorporated herein by reference in its entirety. However, to fix the relationship of the lateral and medial plastic supports to each other and to the boot during the stress of inversion, the plastic side supports are connected by a U-shaped member that wraps around and conforms to the back of the boot. The open end of the U is secured to the boot by a strap that engages the front edge of the heel. In addition, one or more straps on the upper portion of the lateral and medial plastic supports secure the supports in a close relationship to the upper portion of the boot and leg.

The connecting member ideally is made from the same material and molded simultaneously with the lateral and medial plastic side supports. For comfort, the sides of the lateral and medial supports are cushioned with any well-known means such as foam liners or air cells.

Instead of having a U-shaped member integrally formed with the lateral and medial plastic supports that wraps around and conforms to the back of the boot, the U-shaped member may be separate from the lateral and medial side supports and could be adjustably connected for extreme variation in boot size.

Thus it is an important object of the present invention to provide an orthopedic apparatus for use in connection with the outside of a boot to limit the inversion and eversion of the foot while permitting plantarflexion and dorsiflexion thereof.

It is another important object of the present invention to provide a pair of spaced apart side walls for mounting on the outside of the boot and extending longitudinally upwardly to encompass the ankle and lower extremity of the leg above the ankle to enable the ankle to resist inversion and eversion forces. To stabilize the spaced apart side walls with respect to each other, a substantially U-shaped member connects the spaced apart side walls for extending substantially around and conforming to the back of the boot to hold the side walls in fixed relationship to each other and to the boot.

Another important aspect of the present invention is to provide straps that lock the distal end of the brace under the sole at the front of the heel of the boot.

Another important aspect of the present invention is to utilize a cushion between the lateral and medial supports and the boot and leg. The cushion could be a foam liner or an air cell which conforms to the shape of the lateral and medial upright supports.

SUMMARY OF THE INVENTION

Thus the present invention relates to orthopedic apparatus for use in connection with the outside of a boot to limit the inversion and eversion of the foot while permitting plantarflexion and dorsiflexion thereof comprising a pair of spaced apart side walls for mounting on the outside of the boot and extending longitudinally upwardly to encompass the ankle and lower extremity of the leg within the boot to enable the ankle to resist inversion and eversion forces. A substantially U-shaped member connects the spaced apart side walls for extending substantially around and conforming to the back of the shoe to hold the side walls in fixed relationship to each other. Straps are used for removably attaching the connected side walls to the shoe and to the lower extremities of the leg in fixed relationship.

BRIEF DESCRIPTION OF THE DRAWINGS

These and other objects of the present invention will be more completely understood when taken in conjunction with the following detailed description of the drawings in which:

FIG. 1 is an isometric view of the novel orthopedic apparatus including a pair of spaced apart side walls, a substantially U-shaped member connecting the spaced apart side walls and straps serving as the means for removably attaching the connected side walls to a shoe or boot;

FIG. 2 is a side view of the novel orthopedic apparatus attached to the outside of a boot enclosing the lower portion of the leg of the user;

FIG. 3 is an isometric view of an alternate embodiment of the orthopedic apparatus illustrating the side walls connected by a U-shaped member that is adjustable to allow the apparatus to be adapted to variations in shoe sizes.

DETAILED DESCRIPTION OF THE DRAWINGS

Figure 4:
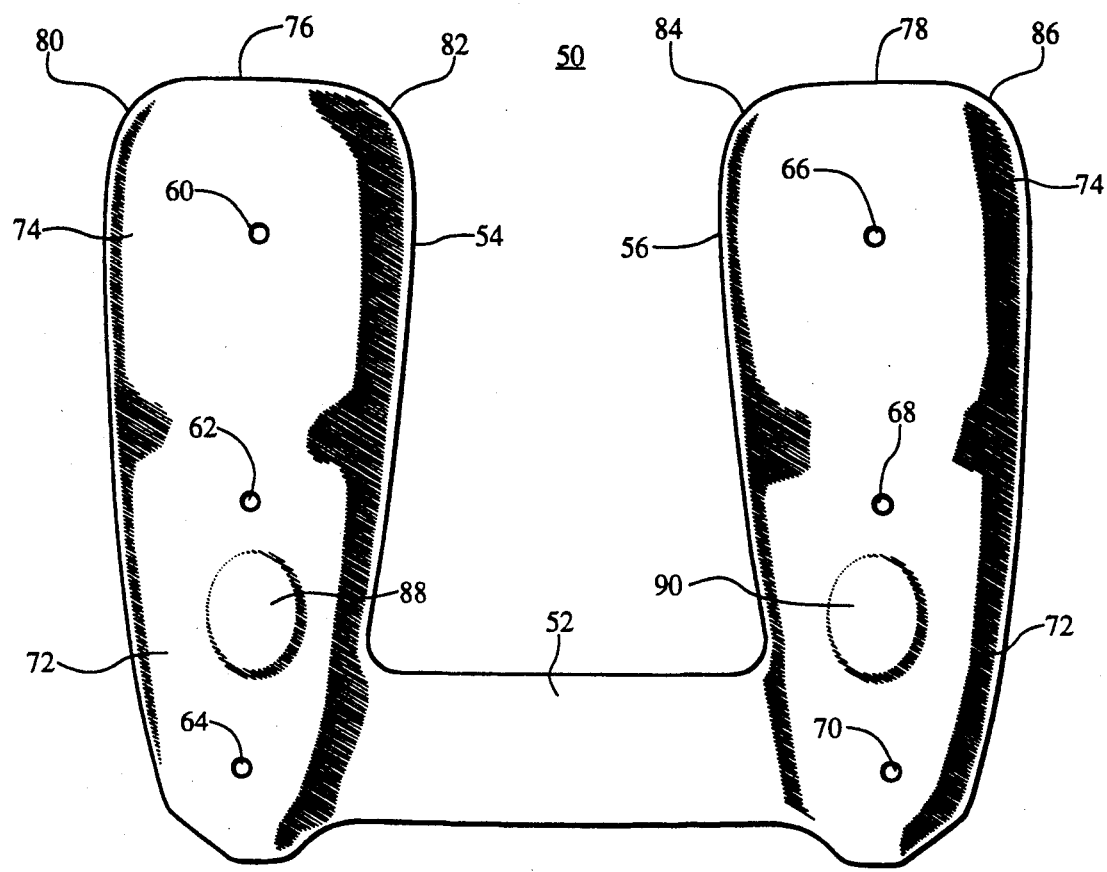
FIG. 4 is a plan view of the novel orthopedic apparatus in its flat state during the formation process prior to the formation of the U-shaped portion connecting the two side walls.

FIG. 1 is an isometric view of the novel orthopedic apparatus to be used in connection with the outside of a shoe to limit inversion and eversion of the foot while permitting plantarflexion and dorsiflexion thereof. As can be seen in FIG. 1, a pair of spaced apart side walls 12 and 14 are connected around the lower portion thereof by a substantially U-shaped member 16 to hold the side walls 12 and 14 in fixed relationship to each other. Straps 18, 20 and 22 are attached to the side walls 12 and 14 in any well-known means as by rivets 24, 26 and 28, respectively, for removably attaching the connected side walls 12 and 14 to a shoe as shown in FIG. 2 enclosing the lower extremities of the leg in fixed relationship.

Thus as can be seen in FIG. 2, which is a side view of the novel orthopedic apparatus mounted on the boot enclosing the leg of a user, the side walls 12 and 14 are mounted on the outside of the shoe 32 and extend longitudinally upwardly to encompass the ankle 38 and lower extremity 34 of the leg 36 above the ankle 38 to enable the ankle 38 to resist inversion and eversion forces. Also as can be seen in FIG. 2, the substantially U-shaped member 16 that connects the spaced apart side walls 12 and 14 extends substantially around and conforms to the back 17 of the shoe 32 to hold the side walls 12 and 14 in fixed relationship to each other. In addition, as can be seen in FIGS. 1, 2 and 3, each side wall 12 and 14 has an arcuate transverse cross-sectional shape sufficient to conform generally to the circumferential contour of the lower leg 34 and the ankle 38. This shape may be more clearly seen in commonly assigned U.S. Pat. No. 4,280,489 which is incorporated herein by reference in its entirety. It will be noted in FIG. 2 that the boot 32 has a shoe portion 33 and an upwardly extending top portion 34 that encompasses the leg above the ankle 38.

As can best be seen in FIG. 4, the width of each side wall portion 12 and 14 gradually tapers from a minimum at the base 72 thereof to a maximum 74 at approximately 4/5 of its longitudinal extent and then decreases in an arcuate fashion along arcs 80, 82, 84 and 86 to the top 76 and 78 thereof. Further, each side wall 12 and 14 includes a recess area 88 and 90 defining a generally oblong shaped cavity for accommodating the corresponding malleolis on the ankle 38.

For further comfort, a cushion 13 and 15 is positioned between each side wall 12 and 14, respectively, and the lower leg 34, including the ankle 38, for comfort. The cushions 13 and 15 may comprise a foam liner or air cells formed of a generally elongated, flattened, inflatable bladder in juxtaposed relationship with each of the side walls 12 and 14 as more fully disclosed in commonly owned U.S. Pat. No. 4,280,489.

As can be clearly seen in FIGS. 1 and 2, the U-shaped member 16 is integrally formed with the side walls 12 and 14 to form a single unit 10. However, as may be more clearly seen in FIG. 3, if desired, the U-shaped member 16 is adjustably connected to the side walls 12 and 14 to allow the apparatus to be adapted to variations in shoe size. Thus in FIG. 3, the U-shaped member may be adjustably connected in any well-known manner such as, for example only, brackets 44 and 46 in which the outer ends of the U-shaped connector member can be inserted and adjusted to fit the particular boot size and then tightened as, for example, by utilizing screws 48 or it may be tightened in any other well-known manner. It is to be understood that the drawing in FIG. 3 is simply diagrammatic in representation. The U-shaped member 16 may have any desired shape and may be attached to the side members 12 and 14 in any well-known manner other than simply brackets 44 and 46 as shown. In addition, any well-known fastening means 48 may also be used to rigidly connect the U-shaped member 16 to the side walls 12 and 14.

Notice also that the straps 18, 20 and 22 illustrated in FIGS. 1 and 2 are all adjustable in length to secure the side walls 12 and 14 in a close relationship to the leg 36 and shoe 32. Thus, detachable hook and loops 30 as shown in FIG. 1 may be used in relationship to any of the adjustable straps 18, 20 and 22. It will be noted that strap 22 passes under the sole of the shoe in the front of the heel 31 of the shoe from one side 12 of the orthopedic apparatus to the other side 14 for fastening. Thus strap 22 locks the distal end of the side walls 12 and 14 under the sole of the shoe at the front of the boot heel 32. The other straps 18 and 20 securely couple the side walls 12 and 14 to the sides 34 of the leg 36 above the ankle. It will be noted that straps 18 and 20 are considerably wider than strap 22. Strap 22 is smaller in width to allow it to securely lock the lower portion or distal portion of the side walls 12 and 14 to the shoe. The wider straps 18 and 20 provide greater comfort and stronger connection of the device 10 to the boot 32. Thus upper strap 18 wraps entirely around the leg and fastens to itself while strap 20 simply passes in front of the ankle from one side wall 12 to the other side wall 14. These wide straps serve to absorb pressure comfortably by the leg.

The side walls 10 and 12 and the U-shaped member 16 are made ideally from the same material and molded simultaneously with the lateral and medial plastic side supports 12 and 14. In such case, the side walls 12 and 14 and the U-shaped member 16 are preferably formed of ⅛″ thickness Kydex plastic as is well known in the art. The side walls and U-shaped member may also be formed of polypropylene having a 0.093″ thickness.

In forming the novel orthopedic apparatus for use with a boot to limit inversion and eversion of the foot, as shown in FIG. 4, the apparatus having lateral and medial side walls 54 and 56 and a U-shaped connecting member 16, molds for the lateral and medial side walls 54 and 56 are positioned opposite from each other in a spaced relationship. A plastic sheet 50 is cut generally in the shape of a U. The cut plastic U-shaped sheet 50 is heated and then the medial and lateral sides 54 and 56 of the heated plastic U are draped on the spaced molds. The molds are then used to form the side walls 12 and 14 of the orthopedic apparatus 10. The formed apparatus is then cooled and removed from the molds. The base 52 of the U, as shown in FIG. 4, is then reheated and is bent over a mold to form a U-shaped member 16 connecting the medial and lateral side walls 12 and 14 at the base thereof.

Thus the present invention provides a prophylactic ankle brace that protects the ankle of paratroopers and fits on the outside of the paratrooper boot so as to make it acceptable to and comfortable for the paratrooper. It includes lateral and medial side walls extending longitudinally upwardly on the outside of the boot to encompass the ankle and lower extremity of the leg above the ankle with a substantially U-shaped member integrally connecting the spaced apart side walls for extending substantially around and conforming to the back of the shoe to hold the side walls in fixed relationship to each other and to the shoe. Straps are provided for removably attaching the connected side walls to the shoe and to the lower extremities of the leg in fixed relationship. One of the straps couples the distal end of the side walls under the shoe and in front of the heel to hold the U-shaped member securely against the heel of the shoe.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. Orthopedic apparatus for use in connection with the outside of a shoe to limit inversion and eversion of the foot while permitting plantarflexion and dorsiflexion thereof comprising:

a pair of spaced apart side walls for mounting on the outside of the shoe and extending longitudinally upwardly to encompass the ankle and lower extremity of the leg above the ankle to enable the ankle to resist inversion and eversion forces;

a substantially U-shaped member connecting the spaced apart side walls and extending substantially around the back outside portion of the shoe surrounding the heel of the foot to hold the side walls in fixed relationship to each other; and means for removably attaching the connected side walls to the shoe and to the lower extremities of the leg in fixed relationship.

2. Orthopedic apparatus as in claim 1 wherein:

each side wall has an arcuate transverse cross-sectional shape sufficient to conform generally to the circumferential contour of the lower leg and ankle; and the width of each side wall portion gradually tapers from a minimum at the base thereof to a maximum at approximately 4/5 of its longitudinal extent and then decreases in an arcuate fashion to the top thereof.

3. Orthopedic apparatus as in claim 2 further including a recess area in each side wall defining a generally oblong shaped cavity for accommodating the corresponding malleolis on the ankle.

4. Orthopedic apparatus as in claim 2 further including a cushion positioned between each side wall and the lower leg, including the ankle, for comfort.

5. Orthopedic apparatus as in claim 4 wherein said cushion comprises a foam liner or an air bag formed of a generally elongated, flattened, inflatable bladder in juxtaposed relationship with each of the side walls.

6. Orthopedic apparatus as in claim 1 wherein said U-shaped member is integrally formed with the side walls to form a single unit.

7. Orthopedic apparatus as in claim 1 wherein said U-shaped member is adjustably connected to the side walls to allow the apparatus to be adapted to variations in shoe size.

8. Orthopedic apparatus as in claim 1 wherein said means for removably attaching the connected side walls to the shoe comprises:

a heel strap having a first width and being removably attached to each side wall for passing under the shoe, in front of the heel, to secure the lower end of the side walls to the shoe; and at least one upper strap attached to the upper portion of the side walls for passing around the lower extremity of the leg above the ankle to secure the upper portion of the side walls to the leg above the ankle.

9. Orthopedic apparatus as in claim 8 wherein all of said straps are adjustable in length to secure the side walls in a close relationship to the leg and shoe.

10. Orthopedic apparatus a in claim 9 wherein the upper strap has a larger width than the heel strap.

11. Orthopedic apparatus as in claim 1 wherein the side walls and U-shaped member are formed of ⅛" thickness Kydex plastic.

12. Orthopedic apparatus as in claim 1 wherein the side walls and U-shaped member are formed of polypropylene having a 0.093" thickness.

* * * * *